(12) United States Patent
Hernandez et al.

(10) Patent No.: US 6,239,277 B1
(45) Date of Patent: May 29, 2001

(54) PROCESS FOR PREPARING PIPERAZINE-SUBSTITUTED ALIPHATIC CARBOXYLATES

(75) Inventors: Pedro E. Hernandez, Schoharie; David John Fairfax, Delmar, both of NY (US); Erik T. Michalson, Charles City, IA (US)

(73) Assignee: Salsbury Chemicals, Inc., Charles City, IA (US)

( * ) Notice: Subject to any disclaimer, the term of this patent is extended or adjusted under 35 U.S.C. 154(b) by 0 days.

(21) Appl. No.: 09/421,514

(22) Filed: Oct. 20, 1999

(51) Int. Cl.$^7$ ............... C07D 295/10; C07D 403/06; A61P 37/08
(52) U.S. Cl. ............ 544/359; 544/396; 544/399
(58) Field of Search ............... 544/359, 399, 544/396

(56) References Cited

U.S. PATENT DOCUMENTS

| | | | |
|---|---|---|---|
| 4,525,358 | * | 6/1985 | Baltes ................................ 514/255 |
| 6,100,400 | * | 8/2000 | Lerman et al. .................... 544/396 |

OTHER PUBLICATIONS

Corey, E. J.; Helal, Christopher J., Tetrahedron Lett. (1996), 37(28), 4837–4840.*
The Condensed Chemical Dictionary, 9th Ed., Gessner G. Hawley Ed., Van Nostrand, New York, p. 638.*

* cited by examiner

Primary Examiner—Mukund J. Shah
Assistant Examiner—Thomas McKenzie

(74) Attorney, Agent, or Firm—Richard J. Hammond

(57) ABSTRACT

A process is disclosed for the preparation of a piperazine-substituted aliphatic carboxylate having the formula

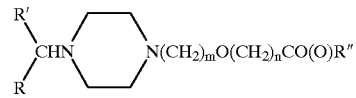

where m and n are individually an integer of from 1 to 6, R and R' are the same or different and are hydrogen, $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or an organic or inorganic cation. The process comprises treating a solution comprising a compound of the formula

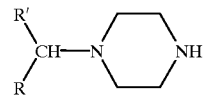

wherein m, R and R' are as defined above and an aliphatic ester of the formula

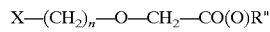

where X is a leaving group and n and R" are as defined above, with an effective amount of a base for a time and at a temperature sufficient to form a piperazine-substituted aliphatic carboxylate. Hydrolysis of the carboxylate with acid produces a piperazine-substituted aliphatic carboxylic acid or the acid salt thereof.

17 Claims, No Drawings

PROCESS FOR PREPARING PIPERAZINE-SUBSTITUTED ALIPHATIC CARBOXYLATES

FIELD OF INVENTION

This invention relates to an improved method for preparing aliphatic esters and carboxylic acids substituted with a substituted piperazine group. More particularly, this invention relates to the preparation of aliphatic carboxylic acids substituted with a 4-aralkylpiperazinyl group.

BACKGROUND OF THE INVENTION

U.S. Pat. No. 4,525,358 discloses the preparation of aliphatic carboxylic acids substituted with 1-alkoxy-4-alkylpiperazines having the formula

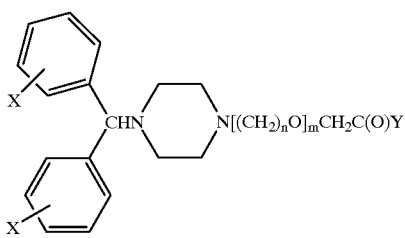

where Y is an ester, hydroxy or amino group, X and X' are independently hydrogen, halo, linear or branched lower alkoxy or trifluoromethyl and m and n are the integers 1 or 2. A number of reaction routes for the preparation of these acetic acid derivatives are shown, e.g., the reaction of 1-(diphenylmethyl)-piperazine with an omega haloacetamide followed by hydrolysis, the reaction of the alkali metal salt of an omega-[4(diphenylmethyl)-1-piperazinyl]alkanol with a 2-haloacetamide followed by hydrolysis, etc.

UK Patent Application 2,225,321, published on May 30, 1990 discloses that 2-[2-[-4-[(4-chlorophenyl)phenylmethyl]-1-piperazinyl]ethoxy]-acetic acid, i.e., the compound shown above where Y is hydroxy, X is hydrogen, X' is chloro and m and n are the integer 1, may be prepared by hydrolyzing 2-[2-[-4-[(4-chlorophenyl)phenylmethyl]-1-piperazinyl]ethoxy]-acetonitrile with base or with acid. The nitrile is prepared by reaction of racemic 1-[(4-chlorophenyl)phenylmethyl]-piperazine with 2-chloroethoxyacetonitrile.

UK Patent Application 2,225,320, published May 30, 1990 discloses the preparation of 2-[2-[-4-[(4-chlorophenyl)phenylmethyl]-1-piperazinyl]ethoxy]-acetic acid by the reaction of 2-[-4-[(4-chlorophenyl)-phenylmethyl]-piperazinyl]1-ethan-1-ol with an alkali metal haloacetate in the presence of an alkali metal alcoholate followed by removal of the alkali metal salt with acid to form the free acid or its acid salt.

In a reaction that uses one of the same starting materials disclosed in the UK '320 application, Polish patent PL 163415 B1 published on Apr. 21, 1992 discloses preparation of 2-[2-[-4-[(4-chlorophenyl)phenylmethyl]-1-piperazinyl]ethoxy]-acetic acid by the reaction of 2-[4-[(4-chlorophenyl)-phenylmethyl]-piperazinyl] 1-ethan-1-ol with chloroacetic acid, in a two phase system that is an organic phase (the substrate and an inert solvent) and an inorganic phase (the hydroxide of an alkali metal in water). A yield of 67% was reported.

Japanese patent application JP 04112852 A2, published Apr. 14, 1992 discloses a method for the preparation of haloalkoxy acetic acid derivatives having the formula

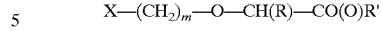

where X is a halide, m is a number between 2 and 7, R is hydrogen or lower alkyl and R' is hydrogen or an ester group. This reference further discloses that the above compound is a useful intermediate for the preparation of Cetirizine [(2-(4-(4-chlorophenyl)phenylmethyl)-1-piperazinyl)ethoxy acetic acid. Details of such preparation are not, however, shown in this reference.

It would be desirable to have synthetic routes for the preparation of the physiologically active compounds similar to those disclosed in U.S. Pat. No. 4,525,358 that result in higher yields or higher purity products.

SUMMARY

A process is disclosed for the preparation of a piperazine-substituted aliphatic carboxylate having the formula

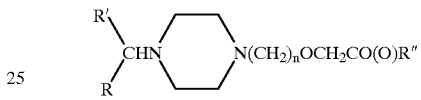

where n is an integer of from 1 to 6, R and R' are the same or different and are hydrogen, $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or a cation. The process comprises treating a substantially anhydrous mixture comprising a compound of the formula

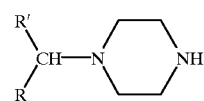

wherein R and R' are as defined above and an alkoxy ester of the formula

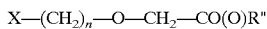

where X is a leaving group and n and R" are as defined above, in the presence of an effective amount of a base for a time and at a temperature sufficient to form a piperazine-substituted aliphatic carboxylate. Hydrolysis of the carboxylate with acid produces a piperazine-substituted aliphatic carboxylic acid or the acid salt thereof.

DESCRIPTION OF THE PREFERRED EMBODIMENTS

In the process of the present invention to prepare a piperazine-substituted aliphatic carboxylate the following definitions apply:

The phrase "$C_1$ to $C_6$ alkyl" is intended to mean and include linear or branched alkyl groups having from one to six carbon atoms such as methyl, ethyl, n-propyl, isopropyl, n-butyl, secondary butyl, tertiary butyl, n-pentyl, 2-methylbutyl, n-hexyl and the like.

The phrase "$C_1$ to $C_6$ alkoxy" is intended to mean and include linear or branched alkoxy groups having from one to six carbon atoms such as methoxy, ethoxy, n-propoxy, isopropoxy, n-butoxy, secondary butoxy, tertiary butoxy, n-pentoxy, 2-methylbutoxy, n-hexyloxy and the like.

The phrase "aryl or heteroaryl that is unsubstituted or substituted with at least one substituent that is halo, $C_1$ to $C_6$ alkyl or $C_1$ to $C_6$ alkoxy" is intended to mean and include the unsubstituted aryl groups such as illustrated by phenyl, 1-naphthyl, 2-naphthyl and the like, the unsubstituted heteroaryl groups such as illustrated by furanyl, thiophenyl, pyrrolyl, pyranyl, pyridinyl and the like as well as the illustrated unsubstituted aryl or heteroaryl groups substituted by at least one halo such as chloro, bromo, etc., $C_1$ to $C_6$ alkyl or $C_1$ to $C_6$ alkoxy such as those shown above.

The phrase "$C_3$ to $C_{12}$ branched alkyl" is intended to mean and include branched alkyl groups having from three to twelve carbon atoms such as isopropyl, 2-methylpropyl, 2-methylbutyl, 2-methylpentyl, 3-methylhexyl, 3-methyloctyl and the like.

The phrase "X is a leaving group" is intended to mean and include leaving groups which are those organic moieties commonly the subject of unimolecular, multistage or bimolecular, concerted elimination reactions and include the moieties illustrated by halo (Cl, Br or I), $OSO_2R$, $OCOR$, $OR$, $NR_3$, $PR_3$, $SR_2$, $SO_2R$, and the like, where R is defined above. Such leaving groups are well known in the prior art.

The word "base" is intended to mean and include an ammonium, alkali metal or alkaline earth metal hydroxide, carbonate or (if appropriate) bicarbonate, hydride or amide such as sodium hydroxide, potassium hydroxide, sodium carbonate, sodium bicarbonate, lithium hydride, sodamide and the like.

The phrase "cation" is intended to mean and include the cation employed to form the base as defined above and includes such cations as sodium, potassium, lithium, ammonium and the like.

The piperazine-substituted aliphatic carboxylates prepared in accordance with the process of the present invention comprises one or more compounds having the following formula

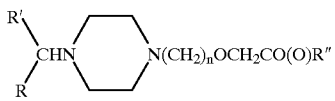

wherein n is an integer from 1 to 6, R and R' are the same or different and are $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or an cation.

In the above piperazine-substituted aliphatic carboxylate compounds it is preferred that n is an integer that is 1 or 2, R and R" are different and are aryl either unsubstituted or substituted with at least one substituent that is methyl, ethyl or chloro and R" is isopropyl, secondary butyl, tertiary butyl or neopentyl. Most preferably, n is 2, R is hydrogen, R' is chloro and R" is tertiary butyl.

The process of the present invention requires that an anhydrous mixture be formed comprising a piperazine compound of the formula

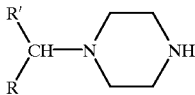

where R and R' are defined above and an ester of the formula $$X-(CH_2)_n-O-CH_2-CO(O)R''$$

where X is a leaving group and n and R" are as defined above.

Preferably, the leaving group in the above ester is halo or an alkyl or aryl sulfonate, most preferably chloro or toluene sulfonate.

The piperazine compound and ester are combined with an effective amount of the base in a substantially anhydrous mixture and heated for a time and at a temperature sufficient to form a piperazine-substituted aliphatic carboxylate. Typically, this temperature is from about 90° to about 150° C., which results in a melt of the components of the mixture. At such temperatures, reaction occurs over a period of from about 5 minutes to about 24 hours, after which the reaction mass is cooled and an inert organic solvent added (with or without water). The carboxylate is obtained usually as a crystalline solid by recrystallization from such solvent.

The bases necessary to effect the reaction of the piperazine compound and the ester are preferably alkali metal or alkaline earth metal hydroxides such as sodium hydroxide or sodium carbonate. These bases are typically used as solids or they may be used as concentrated aqueous solutions, e.g. 15N.

Molar equivalents of ester and piperazine compound are used in the process of the present invention although a slight excess of ester (1.2 to 1.5 equivalents) is sometimes necessary to maximize yields.

In the process of the present invention it is preferred to employ an anhydrous solvent to dissolve the reactants (but not the base) and achieve a more uniform mixture of the compound, the ester and base. Typically such a solvent is inert (it will not react with any of the materials of the reaction mixture) and is readily removed prior to forming the melt as noted above. Removal of such solvent is usually by distillation and a relatively uniform melt residue forms. Such residue may then be heated to the 90° to 150° C. noted above. Solvents of use in this embodiment of the present invention are dimethylformamide, 2-butanone and the like.

The reaction of the present invention produces an aliphatic carboxylate, i.e., a compound where R" is $C_3$ to $C_{12}$ branched alkyl (larger concentrations of the inorganic or inorganic base will produce compounds where R" is an organic or inorganic cation). While physiological active themselves, the compounds produced by the process of this invention are also useful as intermediates for the preparation of other physiologically active materials.

It should be noted that the branched substituent R" causes desirable effects in the production of the subsequent, physiologically active compounds. Thus, higher purity products are produced from the compounds arising from the process of the present invention. Enhanced yields of such products also occurs by use of such branched materials.

The aliphatic carboxylates produced in the process of the present invention may be converted into a compound where R" is —OH(Cetirizine), i.e., 2-[2-[-4-[(4-chlorophenyl) phenylmethyl]-1-piperazinyl]ethoxy]-acetic acid, by base hydrolysis. Typically, this compound is hydrolyzed by base to yield compounds where R" is an organic or inorganic cation depending on the base employed for hydrolysis. Further hydrolysis with acid produces the desired free carboxylic acid. Of course, acid hydrolysis may be used in place of base thereby forming the free carboxylic acid or the acid salt directly. For example, dilute sulfuric acid hydrolysis produces the free carboxylic acid in high yields and good purity. These hydrolysis reactions are well known in the prior art.

The following example are submitted for the purposes of illustration only. They are not intended and should not be regarded as limiting the invention as defined herein in any way.

EXAMPLES

Example 1

A solution of tert-butylbromoacetate (100 g, 5.12 mol) and 2-chloroethanol (495 g, 6.15 mol) in dimethylformamide (1 L) is cooled to −2° C. using a refrigerated circulating bath. Sodium hydroxide (246 g, 6.15 mol) is then added portion-wise so as to maintain the temperature below 10° C. Cooling is discontinued and the reaction is stirred for a total of 6.5 hours, after which the temperature reaches about 22° C. Water (1 L) is added followed by heptanes (3 L). After agitation and settling, the layers are separated. The aqueous phase is re-extracted with 1 L of heptanes and separated. The heptanes extracts are combined, washed with water (1 L), the organic layer separated and the heptanes removed under reduced pressure. A pale yellow oil resulted which is tert-butyl 2-(2-chloroethoxy)acetate, 661 g (66% yield).

Example 2

A suspension of 1-((4-chlorophenyl)phenylmethyl) piperazine (25 g, 90 mmol), tert-butyl 2-(2-chloroethoxy) acetate (19.4 g, 100 mmol) and sodium carbonate (10.6 g, 100 mmol) in dimethylformamide (20 mL) are heated to 110° C. for 4 hours. The resulting reaction mixture is poured into water (50 mL) and extracted with toluene (2×50 mL). The combined organic extracts are washed with water (100 mL). The solvent is removed under reduced pressure to yield a light brown oil which is the tert-butyl ester of 2-[2-[4-[(4-chlorophenyl)phenylmethyl]-1-piperazinyl]ethoxy]-acetic acid (t-butyl cetirizine).

The oil isolated above is suspended in 6N hydrochloric acid (100 mL) and the mixture stirred at room temperature for 8 hours. Ammonium hydroxide, 28%, is added until the pH of the solution became about 8.5. The resulting mixture is treated with methyl tert-butylether (25 mL), causing the mixture to separate into three layers. The two lower layers are separated, re-extracted with methyl tert-butylether (2×25 mL) and the three organic layer-extracts combined, acidified with 37% hydrochloric acid to a pH of about 1 and solid sodium hydroxide added until the pH becomes about 4.2. This mixture is extracted with chloroform (2×100 mL) and the solvent removed under reduced pressure. The residue is dissolved in acetone (200 mL), charcoal (1.0 g) added and the slurry filtered thru a CELITE® filter medium pad. The filtrate is acidified with 37% hydrochloric acid (14.6 mL, 177 mmol) and the solution seeded with several crystals of cetirizine dihydrochloride. The mixture is stirred for 60 hours at room temperature and the precipitate filtered and dried at 0.1 mm Hg at 20–30° C. for 16 hours, affording 23.7 g (57%) of cetirizine dihydrochloride as a white solid.

Example 3

A mixture of t-butyl cetirizine (630 g) and 20% sulfuric acid solution (1250 mL) is heated in a water bath maintained at 65° C. for 2 hours. The reaction mass is cooled and 28% ammonium hydroxide added until a pH of about 8.5 is obtained. The resulting mixture is converted to 420 g (68%) of cetirizine dihydrochloride as disclosed in Example 2.

Example 4

A suspension of 1-((4-chlorophenyl)phenylmethyl) piperazine (260 g, 0.9 mol), tert-butyl 2-(2-chloroethoxy) acetate (195 g, 1.0 mol), sodium hydroxide (106 g, 1 mol) and tert-butyl-ammonium bromide ("TABB", 3.22 g, 0.01 mol, NOTE-TABB is a catalyst for this reaction) is dissolved in 2-butanone ("MEK", 300 mL) heated to 150° C. and the water of reaction azeotroped over a period of about 4 hours. Heating is stopped and to the reaction mixture is added MEK (500 mL) added. The mixture is cooled to ambient, filtered and the solvent removed from the resulting solution by distillation under reduced pressure. The residue is dissolved in methyl tert-butylether (800 mL), washed with water (2×200 mL), saturated sodium chloride (2×100 mL) and the solvent removed under reduced pressure. The residue is treated with hexanes (1.8 mL) to afford tert-butyl (RS) 2-[2-[4-[(4-chlorophenyl)phenylmethyl]-1-piperazinyl] ethoxy]acetate as a white crystalline powder (260 g, 96% yield).

Example 5

The procedure of Example 4 is repeated except that sodium iodide is used in place of TABB. The ester, tert-butyl (RS) 2-[2-[-4-[(4-chlorophenyl)phenylmethyl]-1-piperazinyl]ethoxy]acetate is obtained in 96% yield.

Example 6

The procedure of Example 4 is repeated except that no catalyst is used. The ester, tert-butyl (RS) 2-[2-[-4-[(4-chlorophenyl)phenylmethyl]-1-piperazinyl]ethoxy]acetate is obtained in 91% yield.

Example 7

The procedure of Example 4 is repeated except that water is not removed from the reaction mass by azeotropic distillation. The ester, tert-butyl (RS) 2-[2-[-4-[(4-chlorophenyl) phenylmethyl]-1-piperazinyl]ethoxy]acetate is obtained in 60% yield.

Example 8

A suspension of (RS) 2-[2-[4-[(4-chlorophenyl) phenylmethyl]-1-piperazinyl]ethoxy]acetic acid dihydrochloride (100 g) was dissolved with heating in a water acetone mixture (1:1, 100 mL) until a clear solution is obtained. The clear solution was filtered hot and acetone (1.5 L) is added. The resulting mixture is stirred for 12 hours at ambient temperature and filtered. The filter cake was dried under vacuum for 8 hours. The dried product, purified (RS) 2-[2-[-4-[(4-chlorophenyl)phenylmethyl]-1-piperazinyl] ethoxy]acetic acid dihydrochloride is obtained in 85% yield (85 g).

Example 9

The procedure of Example 8 is repeated except that 1.0 liters of acetone is added to the water:acetone suspension first produced. Purified (RS) 2-[2-[4-[(4-chlorophenyl)-phenylmethyl]-1-piperazinyl]ethoxy]acetic acid dihydrochloride is obtained in 77% yield (77 g).

Example 10

The procedure of Example 9 is repeated except that the water:acetone suspension first produced is used in a 150 mL amount. Purified (RS) 2-[2-[-4-[(4-chlorophenyl)-phenylmethyl]-1-piperazinyl]ethoxy]acetic acid dihydrochloride is obtained in 67% yield (77 g).

Example 11

The procedure of Example 8 is repeated except that 1.6 liters of acetone is added to the water:acetone suspension first produced. Purified (RS) 2-[2-[4-[(4-chlorophenyl)- phenylmethyl]-1-piperazinyl]ethoxy]acetic acid dihydrochloride is obtained in 99% yield (99 g).

Example 12

The procedure of Example 8 is repeated except that acetonitrile is used in place of acetone throughout the purification process. Purified (RS) 2-[2-[-4-[(4-chlorophenyl)-phenylmethyl]-1-piperazinyl]ethoxy]acetic acid dihydrochloride is obtained in 75% yield (75 g).

Example 13

The procedure of Example 8 is repeated except that 2-propanol is used in place of acetone throughout the process. Purified (RS) 2-[2-[-4-[(4-chlorophenyl)-phenylmethyl]-1-piperazinyl]ethoxy]acetic acid dihydrochloride is obtained in 40% yield (40 g).

We claim:

1. A process for preparing a piperazine-substituted carboxylic acid of Formula I

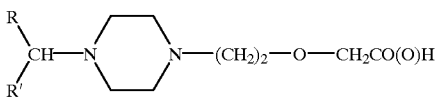

Formula I where R and R' are the same or different and are hydrogen, $C_1$ to $C_6$ alkyl, or aryl or heteroaryl that is unsubstituted or substituted with at least one substituent that is halo, C1 to $C_6$ alkyl or $C_1$ to $C_6$ alkoxy, said process comprising (1) treating a substantially anhydrous mixture comprising (a) an inert solvent (b) a compound of Formula II

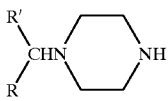

Formula II wherein R and R' are defined above and (c) an aliphatic ester of Formula III

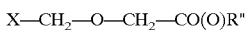

Formula III wherein X is a leaving group and R" is the group

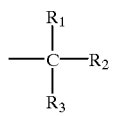

$R_1$, $R_2$ and $R_3$ are the same or different and are C1 to $C_4$ alkyl with the proviso that the sum of the carbon atoms in $R_1$, $R_2$ and $R_3$ does not exceed 11; with an effective amount of a base for a time and at a temperature sufficient to form the compound of Formula IV

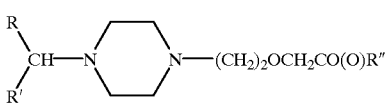

Formula IV wherein R, R' and R" are as defined above and (2) hydrolyzing said compound of Formula IV with sufficient acid to form the compound of Formula I.

2. The process according to claim 1 wherein said base is an alkali metal hydroxide.

3. The process according to claim 2 wherein said base is sodium hydroxide.

4. The process according to claim 3 wherein said inert solvent dissolves said compound of Formula II and said compound of Formula III, but not said base.

5. The process according to claim 4 wherein said solvent is removed from said substantially anhydrous mixture after from about 5 minutes to about 24 hours to form a melt residue.

6. The process according to claim 5 wherein said melt residue is heated to a temperature of from about 90° to about 150° C.

7. The process according to claim 1 wherein R" is tertiary butyl.

8. The process according to claim 7 wherein said base is an alkali metal carbonate.

9. The process according to claim 8 wherein said base is sodium carbonate.

10. The process according to claim 9 wherein said inert solvent dissolves the compound of Formula II and the compound of Formula III, but not said base.

11. The process according to claim 10 wherein said solvent is removed from said substantially anhydrous mixture after from about 5 minutes to about 24 hours to form a melt residue.

12. The process according to claim 11 wherein said melt residue is heated to a temperature of from about 90° to about 150° C.

13. A process for preparing a piperazine-substituted carboxylic acid of Formula I

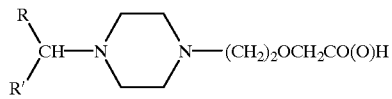

Formula I where R and R" are the same or different and are hydrogen, $C_1$ to $C_6$ alkyl, or aryl or heteroaryl that is unsubstituted or substituted with at least one substituent that is halo, C1 to $C_6$ alkyl or $C_1$ to $C_6$ alkoxy and said process comprising (1) treating a substantially anhydrous mixture comprising (a) an inert solvent (b) a compound of Formula II

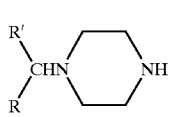

Formula II wherein R and R' are defined above and (c) an aliphatic ester of Formula III

Formula III wherein X is a leaving group and R" is the group

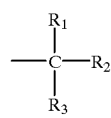

where $R_1$, $R_2$ and $R_3$ are the same or different and are $C_1$ to $C_4$ alkyl with the proviso that the sum of the carbon atoms in $R_1$, $R_2$ and $R_3$ does not exceed 11, in the presence of a catalyst with an effective amount of a base for a time and at a temperature sufficient to form the compound of Formula IV

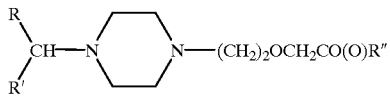
Formula IV wherein R, R' and R'' are as defined above and (2) hydrolyzing said compound of Formula IV with sufficient acid to form the compound of Formula I.

14. The process according to claim 13 wherein said catalyst is sodium iodide.

15. The process according to claim 13 wherein said catalyst is tert-butyl ammonium bromide.

16. A piperazine compound having the formula

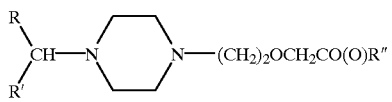

wherein R and R' are the same or different and are hydrogen, $C_1$ to $C_6$ alkyl, or aryl or heteroaryl that is unsubstituted or substituted with at least one substituent that is halo, $C_1$ to $C_6$ alkyl or $C_1$ to $C_6$ alkoxy and R'' is the group

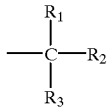

where $R_1$, $R_2$ and $R_3$ are the same or different and are $C_1$ to $C_4$ alkyl with the proviso that the sum of the carbon atoms in $R_1$, $R_2$ and $R_3$ does not exceed 11.

17. The compound according to claim 16 wherein R'' is tertiary butyl.

* * * * *